US00PP34181P2

(12) United States Plant Patent
Bradford et al.

(10) Patent No.: US PP34,181 P2
(45) Date of Patent: May 3, 2022

(54) CHERRY TREE NAMED 'JONRED V'

(50) Latin Name: *Prunus avium*
Varietal Denomination: Jonred V

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 17/300,908

(22) Filed: Dec. 17, 2021

(51) Int. Cl.
*A01H 6/74* (2018.01)
*A01H 5/08* (2018.01)

(52) U.S. Cl.
USPC ..... Plt./181

(58) Field of Classification Search
USPC ..... Plt./181
See application file for complete search history.

(56) References Cited

U.S. PATENT DOCUMENTS

PP12,859 P2 8/2002 Bradford

*Primary Examiner* — Annette H Para

(57) ABSTRACT

The present invention relates to a cherry tree, *Prunus avium*, and more particularly to a new and distinct variety broadly characterized by a medium size, moderately vigorous, hardy, self-unfruitful, and productive tree. The fruit matures under the ecological conditions described in mid May, with first picking on May 12, 2021. The fruit is medium to large in size, very sweet in flavor, oblate in shape, clingstone in type, very firm in texture, deep red in flesh color, blackish red in skin color, and has a moderately long stem that is strongly attached to the fruit.

1 Drawing Sheet

Botanical classification: *Prunus avium.*
Varietal denomination: 'JONRED V'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of cherry tree, which has been denominated varietally as 'Jonred V'.

During a typical blooming season we isolate as seed parents individual cherry trees by covering them with screen houses. A hive of bees is placed inside each such house, and bouquets to provide pollen from different cherry trees are placed in buckets near the trees approximately every two days for the duration of the bloom. During 2010 one such house containing 'Glenred' (U.S. Plant Pat. No. 12,859) cherry tree was crossed by us in this manner. To pollinate this cherry, we selected bouquets from several sources of cherry trees without keeping specific written details. Upon reaching maturity the fruit from this cherry tree was harvested and the seeds were removed, cracked, stratified and germinated as a group with the label 'Glenred House'. They were grown as seedlings on their own root in our greenhouse, and upon reaching dormancy transplanted to a cultivated area of our experimental orchard located near Le Grand, Calif. in Merced County (San Joaquin Valley). During the Summer of 2014 the claimed variety was selected by us as a single tree from the group of seedlings described above. Subsequent to origination of the present variety of cherry tree, we asexually reproduced it by budding and grafting in the experimental orchard described above, and such reproductions were true to the original tree in all respects. The reproduction of the variety included the use of 'Colt' (unpatented) rootstock, upon which the present variety was compatible and true to type.

The present variety is most similar to its seed parent, 'Glenred' (U.S. Plant Pat. No. 12,859) cherry, by being self-unfruitful, by being productive, and by producing medium to large cherries that have a moderately long stem, that mature during the second week of May, and that are oblate in shape, red in flesh color, and fairly crack resistant, but is distinguished therefrom by blooming about four days later and by producing cherries that are darker red in skin color at harvest time, that are firmer in texture, that are sweeter in flavor, and that have a much stronger stem attachment.

SUMMARY OF VARIETY

In summary, the present cherry variety is characterized by a medium size, moderately vigorous, hardy, self-unfruitful, and productive tree. The fruit matures under the ecological conditions described in mid May, with first picking on May 12, 2021. The fruit is medium to large in size, very sweet in flavor, oblate in shape, clingstone in type, very firm in texture, deep red in flesh color, blackish red in skin color, and has a moderately long stem that is strongly attached to the fruit.

DRAWING

The accompanying photograph displays five whole fruits with the stems attached, two whole fruits detached from the stems to exhibit the skin color and form, two sectioned fruits to reveal the flesh, fibers, and stone, two insets depicting flowers and buds, and several leaves, all typical of the subject variety.

POMOLOGICAL CHARACTERISTICS

Referring now more specifically to the pomological characteristics of this new and distinct variety of cherry tree, the following has been observed under the ecological conditions prevailing near Le Grand, Merced County (San Joaquin Valley), Calif., and was developed at the state of firm ripe on May 13, 2021, on the original tree during its eleventh growing season. All major color code designations are by reference to the Inter-Society Color Council, National Bureau of Standards. Common color names are also used occasionally.

PARENTAGE

Seed parent: 'Glenred' cherry (U.S. Plant Pat. No. 12,859).
Pollen parent: Unknown.

TREE

Size: Medium, maintained to a height of 12' [3.66 m.] and a spread of 9' [2.74 m.] after eleven growing seasons utilizing typical pruning.
Vigor: Moderately vigorous, responding typically to irrigation and fertilization. The plant should be grown on a standard commercial rootstock for production purposes.
Growth: Upright.
Form: Vase formed.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Productive.
Fertility: Self-unfruitful, must be cross pollinated by another early to med blooming cherry variety, such as 'Arvin Glen' (U.S. Plant Pat. No. 23,721).
Bearing: Regular, dependent upon seasonal blooming weather.
Leaf bud burst: Toward the end of flowering.
Trunk:
- *Size*.—Medium, reaching a maximum diameter of 6" [152 mm.] after the eleven growing season.
- *Texture*.—Somewhat rough.
- *Bark color*.—A Light grayish reddish brown [45. l.gy.rBr] and Grayish reddish brown [46. gy.rBr] variegation.
- *Lenticels*.—Approximate Number Per Square Inch: 8. Color: Strong yellowish brown [74. s.yBr]. Average Size: Length is 3/8" [9.5 mm.]. The width is typically one fourth as much as the length. Shape: Elongated.

Branches:
- *Size*.—Medium, diameter of main scaffold is 3½" [88.9 mm.] measured 12" above the crotch, diameter of limb is 2" [50.8 mm.] measured 12" above the first fork.
- *Texture*.—Smooth to medium on first and second year wood, increasing roughness with age.
- *Color*.—1st Year Wood topside: Grayish red [19. gy.R]. 1st Year Wood underside: Brilliant yellow green [116. brill.YG]. Older Wood: A Medium gray [265. med.Gy] and Grayish olive [110. gy.Ol] variegation.
- *Lenticels*.—Number Per Square Inch: About 15 on second year wood. Color: Deep orange yellow [69. deep OY]. Average Size: Medium, ⅛" [3.2 mm.] in length. The width is typically one fourth as much as the length. Shape: Elongated.

Leaves:
- *Size*.—Large. Average Length: 5 11/16" [144.5 mm.]. Average Width: 2 13/16" [71.4 mm.].
- *Arrangement*.—Alternate.
- *Thickness*.—Medium.
- *Form*.—Elliptical.
- *Apex*.—Acuminate.
- *Base*.—Rounded.
- *Surface*.—Smooth on both sides.
- *Color*.—Dorsal Surface: Moderate olive green [125. m.OlG]. Ventral Surface: Moderate yellow green [120. m.YG].
- *Red midvein*.—Absent.
- *Margin*.—Finely serrate to serrate.
- *Venation*.—Pinnately net veined.
- *Vein color*.—Light yellow green [119. l.YG].
- *Petiole*.—Average Length: 1⅜" [34.9 mm.]. Average Thickness: 1/16" [1.6 mm.]. Color: Moderate reddish brown [43. m.rBr] on the topside, Light yellow green [119. l.YG] underneath.
- *Stipules*.—Number: 2 per leaf, up to 6 per growing tip. Average Length: ½" [12.7 mm.]. Color: Light yellow green [119. l.YG] turning Moderate olive brown [95. m.OlBr] with age.
- *Glands*.—Number: Usually 2-4 per leaf. Position: Slightly alternate, first pair located on the petiole about ⅛" [3.2 mm.] below the base of blade. Size: Large, 1/16" [1.6 mm.] in length. Form: Oval. Color: Dark reddish orange [38. d.rO] with a Light yellow [86. l.Y] center.
- *Leaf buds*.—Pointed.

Flower buds:
- *Hardiness*.—Hardy with respect to central California blooming season.
- *Diameter*.—Typically 5/16" [7.9 mm.] 3 days before bloom.
- *Length*.—Typically ⅝" [15.9 mm.] 3 days before bloom.
- *Form*.—Not appressed.
- *Surface*.—Very slightly pubescent.
- *Tip color*.—White [263. White].

Flowers: Perfect, complete, perigynous, usually a single pistil, typically about twenty stamens, five sepals and petal locations alternately positioned.
- *Average flower diameter*.—1¾" [44.5 mm.].
- *Average flower depth*.—½" [12.7 mm.] when fully open.
- *Average pedicel length*.—⅜" [9.5 mm.].
- *Number of petals*.—Usually five, a few extra petal fragments occasionally observed.
- *Petal arrangement*.—Overlapping.
- *Petal shape*.—Circular to slightly obovate.
- *Petal margin*.—Somewhat wavy.
- *Average petal diameter*.—11/16" [17.5 mm.].
- *Average petal length*.—11/16" [17.5 mm.].
- *Petal apex*.—Rounded.
- *Petal base*.—Obtuse.
- *Petal color*.—White [263. White] on both sides.

*Anther color*.—Pale orange yellow [73. p.OY].
*Stigma color*.—Vivid greenish yellow [97. v.gY].
*Stigma position*.—Typically located about ⅛" [3.2 mm.] above the nearby anthers.
*Stamen position*.—Typically located about 1/32" [0.8 mm.] below the petals.
*Ovary*.—Non-pubescent.
*Sepal color*.—Light grayish purplish red [261. l.gy.pR] over Light yellow green [119. l.YG] on the outer surface. The inner surface is Light yellow green [119. l.YG].
*Sepal outer surface*.—Slightly pubescent.
*Sepal length*.—⅜" [9.5 mm.].
*Sepal width*.—3/16" [4.8 mm.].
*Sepal apex*.—Elliptical to match the sepal length and width.
*Sepal margin*.—Fairly smooth.
*Average pistil length*.—¾" [19.1 mm.].
*Average stamen length*.—9/16" [14.3 mm.].
*Fragrance*.—Moderate.
*Pollen production*.—Moderate.
*Pollen color*.—Strong yellow [84. s.Y].
*Bloom density*.—Heavy.
*Blooming period*.—Medium, blooms four days later than 'Glenred' (U.S. Plant Pat. No. 12,859) cherry.
*Onset of bloom*.—One percent on Mar. 13, 2021.
*Date of full bloom*.—Mar. 26, 2021.
*Duration of bloom*.—One to two weeks, dependent on ambient temperature.
*Number per cluster*.—Usually 2 to 6, 3 average.

FRUIT

Maturity when described: Firm ripe, May 15, 2021.
Date of first picking: May 12, 2021.
Date of last picking: May 21, 2021.
Size: Uniform, medium to large.
*Average diameter axially*.—1⅛" [28.6 mm.].
*Average diameter across cheek plane*.—1¼" [31.8 mm.].
*Average diameter across suture plane*.—1" [25.4 mm.].
*Typical weight*.—0.40 ounces [11.3 grams].
Form: Uniform, symmetrical, oblate.
*Axial view form*.—Oblate.
*Suture plane form*.—Oblong.
*Cheek plane form*.—Oblate.
Suture: Very inconspicuous, extending from the base to just beyond the pistil point.
*Near the base*.—A shallow trough.
*Along the side*.—Very flat to slightly bulging.
*Near the apex*.—A shallow groove.
Ventral surface: Rounded, virtually no lips.
Lips: None on most.
Cavity: Flaring, suture showing on one side.
*Depth*.—3/16" [4.8 mm.].
*Breadth*.—9/16" [14.3 mm.].
Base: Rounded to truncate, cordate if viewed parallel to the suture.
Apex: Rounded to truncate, cordate if viewed parallel to the suture.
Pistil point: A Grayish yellowish [90. gy.Y] dot.
Stem: Medium to long.
*Average length*.—1 9/16" [39.7 mm.].
*Average width*.—1/16" [1.6 mm.].
*Attachment*.—Strong.
Skin:
*Thickness*.—Medium.
*Surface*.—Smooth.
*Tenacity*.—Tenacious to the flesh.
*Astringency*.—Slight.
*Tendency to crack*.—Very slight.
*Color*.—Blackish red [21. blackish R] over a Very deep red [14. v.deep R] background.
Flesh:
*Color*.—Very deep red [14. v.deep R] toward the skin and stone, Moderate red [15. m.R] in the center, Light grayish red [18. l.gy.R] fibers throughout.
*Surface of pit cavity*.—Covered with Very dark red [17. v.d.R] fibers when twisted from the stone.
*Amygdalin*.—Slight.
*Juice*.—Abundant, rich.
*Juice color*.—Very deep red [14. v.deep R].
*Texture*.—Firm, crisp.
*Fibers*.—Abundant, fine, tender.
*Ripens*.—Fairly even.
*Flavor*.—A very tasty blend of acid and sugar, typically 26 brix.
*Aroma*.—Very slight.
*Eating quality*.—Excellent.

STONE

Type: Clingstone.
Form: Globose.
Hilum: Narrow, oblong.
Base: Rounded.
Apex: Acute.
Sides: Fairly equal.
Surface: Fairly smooth.
External color of stone: Light yellowish brown [76. l.yBr].
Pit wall color when cracked: Pale orange yellow [73. p.OY].
Cavity surface color: Strong yellowish brown [74. s.yBr].
Average pit wall thickness: 1/16" [1.6 mm.].
Average length: 7/16" [11.1 mm.].
Average width: ⅜" [9.5 mm.].
Average breadth: ⅜" [9.5 mm.].
Tendency to split: None observed.
Kernel:
*Form*.—Oval.
*Skin color*.—Yellowish white [92. yWhite] when first removed.
*Pellicle color*.—Strong brown [55. s.Br].
*Taste*.—Bitter.
*Viable*.—Yes.
*Average length*.—5/16" [7.9 mm.].
*Average width*.—¼" [6.4 mm.].
*Amygdalin*.—Strong.

USE

Market: Fresh market and long distance shipping.
Keeping quality: Good, fruit quality observed to remain in good condition after 14 days in standard cold room at 36° Fahrenheit [2° Celsius].
Shipping quality: Good.
Resistance to insects: Not tested.
Resistance to diseases: Not tested.

OTHER NOTES

Although the new variety of cherry tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of cherry tree, substantially as illustrated and described.

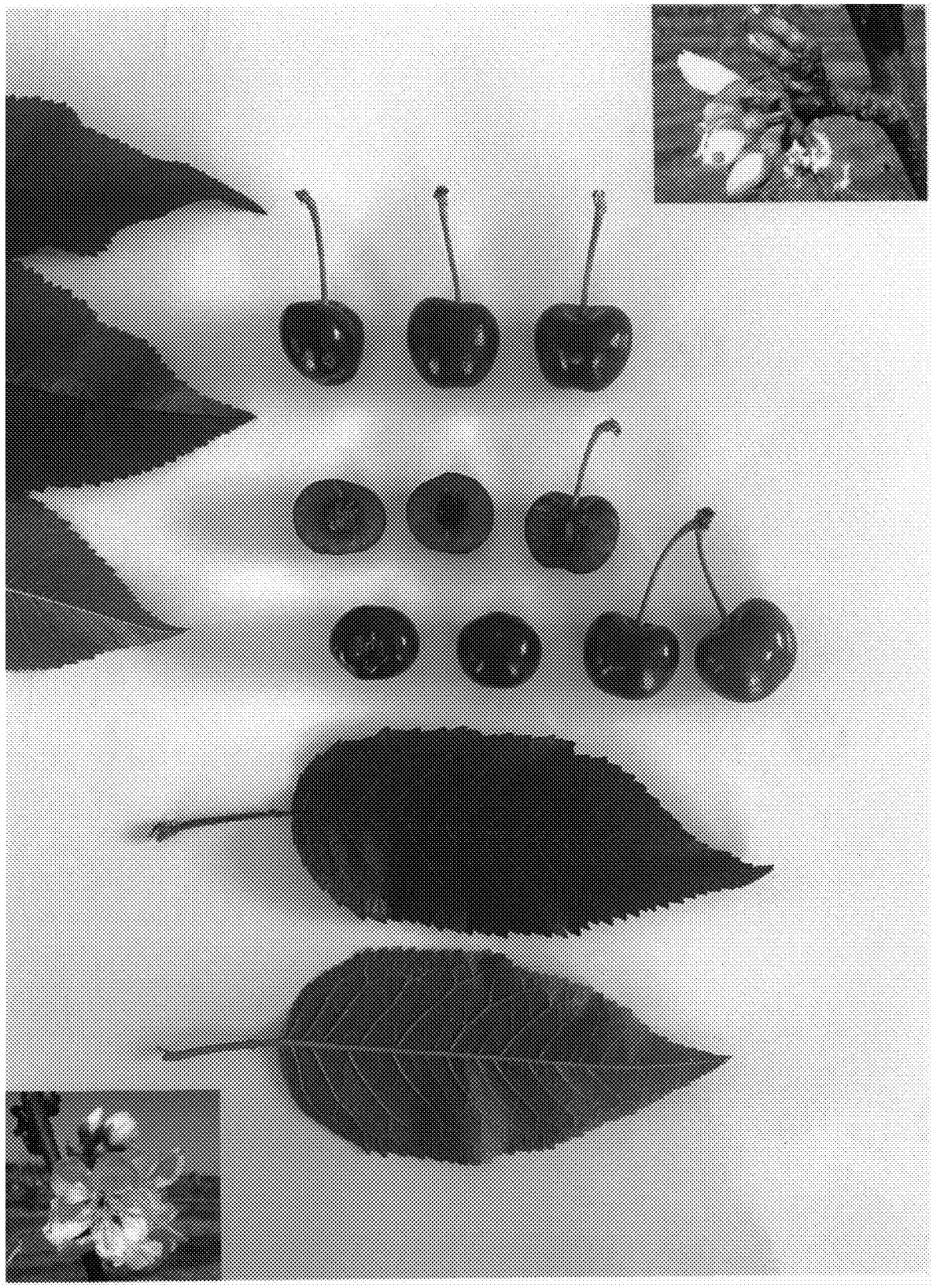

* * * * *